United States Patent [19]

Kendall et al.

[11] Patent Number: 4,994,492

[45] Date of Patent: Feb. 19, 1991

[54] TREATMENT OF MELANOMA USING N,N-DIMETHYLGLYCINE

[75] Inventors: Roger V. Kendall, Williston, Vt.; John W. Lawson, Clemson; Elizabeth A. Reap, Pendleton, both of S.C.

[73] Assignee: Foodscience Corporation, Essex Junction, Vt.

[21] Appl. No.: 294,845

[22] Filed: Jan. 9, 1989

[51] Int. Cl.$^5$ ............................................ A61K 31/195
[52] U.S. Cl. ..................................................... 514/561
[58] Field of Search ......................................... 514/561

[56] References Cited

U.S. PATENT DOCUMENTS 4,385,068  5/1983  Kendall et al. ...................... 514/561

FOREIGN PATENT DOCUMENTS 1151065  8/1983  Canada ................................. 514/561

OTHER PUBLICATIONS

Passwater, Richard A., *Let's Live Magazine,* "Dimethylglycine Update, New Studies Confirm DMG Improves Health", Feb. 1987.

*Primary Examiner*—Jerome D. Goldberg
*Attorney, Agent, or Firm*—Millen, White & Zelano

[57] ABSTRACT

This invention relates to a method for inhibiting the metastasis or formation of a melanoma tumor by treating the patient with an effective amount of N,N-Dimethylglycine.

5 Claims, No Drawings

TREATMENT OF MELANOMA USING N,N-DIMETHYLGLYCINE

BACKGROUND OF THE INVENTION

This invention relates to the use of N,N-dimethylglycine (DMG) to treat melanoma tumors in man or animals.

Dimethylglycine is an intermediary metabolite and amino acid found in low levels in many foods, and is produced in the body from choline. DMG is an endogenous compound and an enzyme system in the body effectively converts the substance into metabolites that are either used by the body or are safely excreted from the body.

A great deal of research has been carried out in recent years on the physiological effects of N,N-dimethylglycine.

Referring to previous work, U.S. Pat. No. 4,385,068, issued 5/24/83 discloses treating irradiated animals with a derivative of this compound to alleviate the effects of excess radiation on the immune system. The stated object of the invention of U.S. Pat. No. 4,385,068 is (a) to provide a method to enhance one or both of the cell-mediated response and humoral response of the body; (b) to provide a method whereby the deliberately induced production of antibody artificially acquired in a living organism can be enhanced, and (c) to provide a method to increase the amount of antibody production and/or decrease the time of antibody production in the deliberately induced production of antibodies in a living organism. According to the patent, the DMG is administered so that the immunological response of the living organism is potentiated when exposed to an antigen in a natural environment and/or when deliberately exposed, or exposed to a subject after the subject has been exposed to a disease agent having an antigenic component in a natural environment in order to aid the host in responding to the naturally occurring infection.

The literature is also replete with articles concerning N,N-dimethylglycine and its potential uses.

At the 1980 Pacific Slope Biochemical Conference a paper entitled "Decrease of Lactic Acid Concentration in Blood of Animals Given N,N-Dimethylglycine" was presented. This research a the nutritional evaluation as a result of a 157-day subchronical estimation of N,N-dimethylglycine toxicity. This study also indicated that a decreased lactic acid production by male New Zealand white rabbits exposed to severe surgical stress by administering intravenously dimethylglycine. High-dose rats showed better adaptation to hypoxia subchronical toxicity tests.

In the January, 1981, issue of The Journal of Infectious Diseases, Vol. 143, No. 1, an article entitled "Immunomodulating Properties of Dimethylglycine in Humans", discussed the fact that dimethylglycine is an immunomodulator, if not an immunoadjuvant in humans (since the latter term is reserved for parenterally administered substances that are incorporated or injected simultaneously with an antigen). The normalization of mitogenic responsiveness by lymphocytes from patients with sickle cell disease and diabetes was tested. In both groups, the blast transformation activity of lymphocytes treated with DMG and exposed to three lectins was approximately doubled. Preliminary data suggest, according to the authors, that DMG is both a humoral and cellular immunomodulator, and might have great use with vaccines for intracellular infections and certain parasitic diseases. The article also states, "In addition, it should be tested for its effects on spontaneously occurring tumors in animals in which many of the immune parameters influencing tumor growth are known. Because DMG is nontoxic and can be given orally, it would seem to have obvious advantages over the oil-in-water adjuvants now contemplated for use in patients with cancer in conjunction with tumor associated antigen vaccines." There is no suggestion of dosage ranges or mode of application for DMG or that it would actually be effective for the treatment of any particular type of tumor.

The March, 1982, issue of Equine Practice contains an article entitled "Effect of a Nutritional Supplement Containing N,N-Dimethylglycine (DMG) on the Racing Standardbred." This article discloses that research showed that DMG can increase oxygen utilization and thereby decrease lactic acid levels in animals under extreme stress. The article also discusses the finding that human tests indicated an increase in exhaustion time, and an enhancement of the body's immune response, both by increasing the antibody production and lymphocyte generation by the administration of DMG. The tests reported in this article indicated that the inclusion of DMG in the diet of the racing Standardbred is responsible for a lower blood lactic acid level following training. Trainers found the horses to be more aggressive, to have better appetites and attitudes and to recover faster from racing and training than the controls.

The November-December, 1982, issue of Canine Practice contains an article entitled "A Clinical Evaluation of N,N-Dimethylglycine (DMG) and Diisopropylammonium Dichloroacetate (DIPA) on the Performance of Racing Greyhounds".

This article summarized the biological reactions of dimethylglycine in three broad categories: Transmethylation, cellular respiration, and hepatic function. The study that was the subject of the article indicated that improvement in racing performance was found when greyhounds were given DMG, and also stated that they showed better recovery after races with less fatigue or muscle stiffness. Additional clinical applications of DMG, including exertional rhabdomyolysis (inflammatory change in the muscle fibers of the longissimus group), muscular cramp, and hepato-pathology were discussed.

In the February, 1987, issue of Let's Live Magazine, an article entitled "DIMETHYLGLYCINE UPDATE, New Studies Confirm DMG Improves Health" states that the benefit of enhanced immunity is protection against diseases ranging from cancer and AIDS to minor diseases such as influenza. The article states that DMG is a metabolic enhancer, acts as a detoxifying agent and antioxidant, and is a versatile normalizer of physiological functions. The article also discusses the fact that the immune system is a complex network of white blood cells and molecular compounds, such as antibodies and interferon. There are two types of white blood cells—lymphocytes and macrophages. The immune system produces three types of lymphocytes: T cells, B cells, and K cells. Interferon is an antiviral, antitumor compound produced from T cells. The article indicates that T cells identify and reject foreign matter, while B cells produce antibodies. The article states that little is understood about the killer K cells, which can attack tumor cells directly. The article further states that early research showed that DMG stimulates B cells to produce much higher antibody responses (humoral branch) and potentiates the activity of T cells and macrophages (cellular immunity branch).

The article also states that the DMG was effective in doubling interferon production, and that further work is underway to evaluate DMG's effect on K cells, the body's principal defense mechanism against tumor cells. The article also alludes to a related line of research which indicated that the methyl-group donating ability of DMG is protective against cancer. As stated by the author, "I have already discussed the fact that DMG is not mutagenic or carcinogenic but, rather, is actually protective against mutagens and cancer."

In the February, 1987, issue of Health Consciousness, an article entitled "N,N-Dimethylglycine and the Immune Response" reviewed the prior research in the effect of DMG on the body, and also indicated that DMG will increase interferon production. The article states that DMG is an oral immune stimulating nutrient which can offer individuals increased resistance to and recovery from infectious diseases, and stated that depressed immunity is associated with most degenerative diseases such as cancer, diabetes and cardiovascular disease.

At the 1987 ASM Annual Meeting, a paper entitled "The Effect of DMG on the Immune Response of Rabbits" was presented. This paper concluded that DMG can affect the cellular branch of the immune system by lymphocyte activation. Lymphocytes from DMG fed animals can stimulate the cellular immune system by lymphatic proliferation. During primary response, high levels of interferon was present in the DMG fed animals, regardless of the immunogen source. No interferon was detected in immunized control animals not fed DMG. Interferon was not present in samples obtained following the secondary response.

In an article entitled "DMG, Properties and Proprieties" published in The Blood Horse on June 27, 1987, research on humans was discussed which showed that DMG stimulated B-cells produce much higher antibody responses and that it also enhances the activity of T cells and macrophages.

It has now been found that DMG is an effective agent for the treatment of tumors, particularly the prevention of the metastasis of melanoma tumors.

OBJECTS OF THE INVENTION

It is an object of this invention to provide a method of treating melanoma tumors.

It is another object of this invention to provide a method for retarding and reducing growth of melanoma tumors.

It is a further object of this invention to provide a method for preventing or reducing metastasis from the primary tumor site of melanoma tumors.

It is still another object of this invention to provide a method for increasing lymphocyte infiltration and walling off (fibroblast activity) of the primary tumor site of melanoma tumors.

SUMMARY OF THE INVENTION

The above and other objects are obtained by administering N,N-dimethylglycine to a living organism in an amount sufficient to achieve the desired results.

In one aspect, this invention relates to a method of inhibiting the metastasis of a melanoma tumor comprising administering to a patient with a melanoma tumor a metastasis-inhibiting amount of N,N-dimethylglycine or a pharmaceutically acceptable salt thereof.

Upon further study of the specification and appended claims, further objects and advantages of this invention will become apparent to those skilled in the art.

DETAILED DESCRIPTION OF THE INVENTION

It has now been found that N,N-Dimethylglycine, a compound of the formula:

$(CH_3)_2NCH_2COOH$ or a pharmacologically acceptable salt thereof, can be used to treat melanoma tumors, whereby DMG can help contain metastasis of the tumor.

Melanoma is an uncommon form of skin cancer, which is highly metastatic in nature. Due to its highly metastatic nature, death almost invariably ensues before the cancer can be stopped. When the cancer is finally detected, in most cases it has already spread throughout the body. Thus, it is desirable to find an agent which will serve to alleviate the metastasis of the tumor, thus increasing the patient's chance of survival. It has now been found that DMG plays a role in inhibiting B-16 melanoma metastasis in mice and in retarding tumor growth in the well established model. Studies in mice have also shown that DMG may prevent the formation of tumors and/or slow down their appearance.

Dimethylglycine is a relatively non toxic substance. It was found by researchers that in the rat, DMG-HCl has an acute $LD_{50}$ toxicity when administered orally as a neutralized aqueous solution of 7.4 g/kg of body weight; 6 g/kg when administered intraperitoneally, and 5.4 g/kg when administered subcutaneously in mice.

The treatment of the instant invention involves the administration of DMG or a pharmaceutically acceptable salt thereof to a subject, including but not limited to mammals, including humans.

One aspect of this invention involves administering to a patient, e.g. human who has been diagnosed as having melanoma. It is preferred that the tumor has not yet metastasized. DMG should be administered as soon as possible even though the cancer or suspected cancer has not been fully characterized. Clinical experience indicates that DMG will not interfere with most other drug therapies generally and can be given to patients regardless of age, sex, cancer type or general health status either by oral or IV routes. DMG can be expected to improve the immune status of cancer patients with melanoma in 7–10 days. Positive evidence in treatment against the tumor should be evident in 14–28 days.

The DMG used in the instant invention can be processed in accordance with conventional methods of galenic pharmacy to produce medicinal agents for administration to patients, e.g. mammals, including humans.

The DMG used in this invention can be employed in admixture with conventional excipients, i.e. pharmaceutically acceptable organic or inorganic carrier substances suitable for parenteral, enteral (e.g., oral) application which do not deleteriously react with the active compound. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g. lubricants, preservatives, stabilizers, wetting agents emulsifiers, salts for influencing osmotic pressure, buffers, coloring, flavoring and/or aromatic substances and the like which do not deleteriously react with the active compound. They can also be combined where desired with other active agents.

For parenteral application, particularly suitable are injectable, sterile solutions, preferably oily or aqueous solutions, as well as suspensions, emulsions, or implants. Ampoules are convenient unit dosages.

For enteral application, particularly suitable are tablets, dragees, liquids, drops, or capsules.

Generally, when used in the inhibition of metastasis of the melanoma tumor, the compounds of this invention are dispensed in unit dosage form comprising 1–100 mg/kg, preferably 20–80 mg/kg in a pharmaceutically acceptable carrier per unit dosage.

The daily dosage of the compounds according to this invention, when used to prevent metastasis or prevent the formation of melanoma tumor is generally about 1–500 mg/kg/day, preferably 10–100 mg/kg/day. When administered orally, the dosage can be in a single or divided dosages every 2–24 hours, preferably every 4 hours; when administered intraperitoneally or intramuscularly initially it should be administered daily, and thereafter periodically, preferably at least every third day.

DMG is also effective in potentiating or improving the immune system or resistance of a host diagnosed as having a melanoma tumor, including B and T cell proliferation and activity, lymphokine production such as interferon and macrophage activity. DMG acts as an immune modulator to increase survival time. DMG also acts to retard and reduce tumor growth, and increase lymphocyte infiltration and walling off (fibroblast activity) of the primary tumor site. When used to treat these indications, a dosage range of 0.1 mg to 500 mg/kg/day should be used.

DMG can be administered concurrently or alternately with other therapeutic treatments conventionally employed in cancer therapy, e.g. irradiation, surgery, chemotherapeutic agents, and other acceptable therapies designed to reduce the tumor load.

It will be appreciated that the actual preferred amounts of active compound in a specific case will vary according to the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, are hereby incorporated by reference.

EXAMPLES

Twenty-one C57BL/6 mice from Charles River Co. were divided randomly into three groups containing seven mice per group. The average weight of the mice was 13 grams. Mice in Group 1 received 100/mg/kg body weight of DMG dissolved in 0.2 cc $dH_2O$ by intraperitoneal injections everyday beginning seven days prior to the injection of B-16 melanoma cells into the shoulder pad. The administration of DMG was continued throughout the duration of the experiment. Mice in Group 2 (7 mice) began receiving DMG injections on the same day as the B-16 cell injections. The DMG injections were then also continued throughout the experiment. Group 3 (7 mice) received only the B-16 cells and no DMG. However, water injections were given everyday to this group. The four week old mice all received 0.2 cc of $1 \times 10^6$ cells/ml of B-16 melanoma cells, subcutaneously at the nape of the neck.

The B-16 mouse melanoma cultures were incubated at 37° C. in 25 $cm^2$ Falcon flasks with 5.0 ml of antibiotic free Minimal Essential Medium (MEM) containing 10% (v/v) fetal bovine serum. Cells were removed from the flasks with versene and resuspended in PBS on the day of injection.

The mice were monitored everyday for the presence of tumor, and the size of the tumor recorded. The mice that died during the experiment were dissected and tissue samples obtained for histological analysis. All surviving animals were sacrificed seven weeks after the injection of B-16 cells. The samples obtained were fixed in 10% formalin, processed by a tissue processor and a standard hematoxylin and eosin stain was done on the slide sections. The stained slides were analyzed by a pathologist. The pathology report is depicted in Table 1.

RESULTS.

Fourteen days after injection the first visible tumor was observed in Group 1. On day 15, the second tumor was seen in Group 1. On Day 16 the third visible tumor was observed in Group 1. On Day 18 the first tumor was observed in the B-16 control group 3. Table 2 depicts the time between the first appearance of the tumor in the test mice and the record of its death. Table 3 depicts the interval between tumor sighting and death.

On Day 53, all surviving mice were sacrificed as tabulated in Table 4. From the table, it can be seen that two mice from Group 1 and Group 2 died during the experiment. Five mice died from Group 3.

In Group 3, five out of seven mice developed tumors. In Group 1, only two mice developed tumors. Table 4 depicts the tumor size at death or at the time of sacrifice of the animal.

In Group 1 in every mouse with a tumor nodule, no matter how large, there was no metastasis to any organ. In Group 2, the same thing was seen; the mice had tumor nodules but no metastasis. (mouse 2–7 had questionable metastasis to lymph nodes, however). In Group 1 lymphocytic activity was seen in the mice with large subcutaneous tumors. In Group 2 mice with large tumors also showed lymphocytic infiltrates. In contrast, the B-16 control group 3, metastatic lesions were observed in the heart, lungs, and mediastinum in most of the mice with tumors. This was the only group of mice where metastasis to any organ was seen. This is shown in Table 1.

In the DMG-treated mice, there was more lymphocytic involvement near the tumor than in the B-16 control group. In one DMG treated mouse, lymphocytic migration to the tumor area was observed.

The fact that larger tumors appeared earlier, as shown in Table 4, in the DMG groups than in the B-16 control groups suggests that the tumor was localized by the immune cells with the aid of DMG. This would also account for the fact that DMG mice lived longer than the B-16 mice. If a true, localized response is seen, the use of DMG would allow for earlier and easier detection. Thus, methods to rid the body of the tumor before it begins to metastasize could be implemented. As can be seen in Table 4, the number of mice in the DMG-treated groups that actually got palpable tumors was less than the number of tumors in the B-16 control group. There was no difference in the number of tumors developing in Group 1 and Group 2, however, the nodules were larger in Group 2, indicating that DMG may also reduce the susceptibility of the animal to B-16 melanoma by immuno-enhancing the immune system.

TABLE 1

Results of the Pathology Report

| Mouse I.D. | Subcutaneous Nodule | Metastasis Lung | Heart | Liver | Kidney | Observations |
|---|---|---|---|---|---|---|
| 1-1 | 0 | 0 | 0 | 0 | 0 | |
| 1-2 | 0 | 0 | 0 | 0 | 0 | |
| 1-3 | 0 | 0 | 0 | 0 | 0 | |
| 1-4 | + | 0 | 0 | 0 | 0 | Spleen enlarged |
| 1-5 | 2+ | 0 | 0 | 0 | 0 | |
| 1-6 | 0 | 0 | 0 | 0 | 0 | |
| 1-7 | 2+ | 0 | 0 | 0 | 0 | |
| 2-1 | 0 | 0 | 0 | 0 | 0 | |
| 2-2 | 0 | 0 | 0 | 0 | 0 | |
| 2-3 | 2+ | 0 | 0 | 0 | 0 | Lymphocytic infiltrates |
| 2-4 | 0 | 0 | 0 | 0 | 0 | |
| 2-5 | 2+ | 0 | 0 | 0 | 0 | |
| 2-6 | 0 | 0 | 0 | 0 | 0 | |
| 2-7 | 2+ | 0 | 0 | 0 | 0 | Spleen enlarged Possible mets to lymph node |
| 3-1 | 0 | 0 | 0 | 0 | 0 | |
| 3-2 | 0 | 0 | 0 | 0 | 0 | Small mets to lymph node, mast cell infiltration |
| 3-3 | + | + | + | + | + | + Mets, Heart necrosis |
| 3-4 | | (organs not well-preserved) | | | | |
| 3-5 | + | + | + | 0 | 0 | + Mets to lungs, heart and mediastinum |
| 3-6 | + | 0 | 0 | 0 | 0 | |
| 3-7 | 0 | 0 | 0 | 0 | 0 | |

TABLE 2

First Appearance of Tumor in Mice and Record of Death

| Day | Procedure or Observation | Groups |
|---|---|---|
| 1 | Inject B-16 Cells in all | 1, 2, 3 |
| 13 | Tumor in Mouse 2-5 | 2 |
| 14 | Tumor in Mouse 1-3 | 1 |
| 16 | Tumor in Mouse 1-7 | 1 |
| | Tumor in Mouse 2-3 | 2 |
| 18 | Tumor in Mouse 3-5 | 3 |
| 23 | Death in Mouse 1-3 | 1 |
| 24 | Tumor in Mouse 1-4 | 1 |
| 25 | Tumor in Mouse 3-6 | 3 |
| | Tumor in Mouse 3-7 | 3 |
| 27 | Tumor in Mouse 3-3 | 3 |

TABLE 2-continued

First Appearance of Tumor in Mice and Record of Death

| Day | Procedure or Observation | Groups |
|---|---|---|
| | Tumor in Mouse 3-4 | 3 |
| | Tumor in Mouse 2-7 | 2 |
| 32 | Death in Mouse 2-5 | 2 |
| 35 | Death in Mouse 3-5 | 3 |
| 41 | Death in Mouse 1-7 | 1 |
| | Death in Mouse 3-3 | 3 |
| | Death in Mouse 3-4 | 3 |
| | Death in Mouse 2-3 | 2 |
| 45 | Death in Mouse 3-6 | 3 |
| | Death in Mouse 3-7 | 3 |

TABLE 3

Mice Surviving at End of Experiment (each group originated with 7 mice)

| Group | No. of Mice Remaining | No. of Mice Remaining With Visible Tumors |
|---|---|---|
| 1-DMG | 5 | 1 |
| 2-DMG | 5 | 1 |
| 3-B-16 | 2 | 5 |

TABLE 4

Record of Tumor Size at Death or Sacrifice of Animals

| Group | Mouse | Status | Tumor | Tumor Measurement L × W × H (cm) |
|---|---|---|---|---|
| 1 | 1-1 | Live | None | |
| | 1-2 | Live | None | |
| | 1-3 | Dead | Yes | |
| | 1-4 | Live | Yes | 4.5 × 4.1 × 2.5 |
| | 1-5 | Live | None | |
| | 1-6 | Live | None | |
| | 1-7 | Dead | Yes | 4.0 × 2.2 × 2.8 |
| 2 | 2-1 | Live | None | |
| | 2-2 | Live | None | |
| | 2-3 | Dead | Yes | 4.5 × 3.0 × 3.6 |
| | 2-4 | Live | None | |
| | 2-5 | Dead | Yes | 7.7 × 1.5 × 4.9 |

TABLE 4-continued

Record of Tumor Size at Death or Sacrifice of Animals

| Group | Mouse | Status | Tumor | Tumor Measurement L × W × H (cm) |
|---|---|---|---|---|
| | 2-6 | Live | None | |
| | 2-7 | Live | Yes | 4.2 × 4.0 × 2.8 |
| 3 | 3-1 | Live | None | |
| | 3-2 | Live | None | |
| | 3-3 | Dead | Yes | 1.8 × 1.5 × 1.0 |
| | 3-4 | Dead | Yes | 3.0 × 3.5 × 3.4 |
| | 3-5 | Dead | Yes | 4.5 × 3.2 × 2.0 |
| | 3-6 | Dead | Yes | 4.2 × 3.4 × 2.9 |
| | 3-7 | Dead | Yes | 4.6 × 3.5 × 3.4 |

The preceding examples can be repeated with similar success by substituting the generically or specifically described coatings of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of inhibiting the metastasis of a melanoma tumor comprising administering to a patient with a melanoma tumor a metastasis-inhibiting amount of N,N-dimethylglycine or a pharmaceutically acceptable salt thereof.

2. A method according to claim 1, wherein the Dimethylglycine is administered systemically.

3. A method according to claim 2, wherein the N,N-dimethylglycine is administered orally.

4. A method according to claim 1, wherein the N,N-dimethylglycine is administered in an amount of 1-500 mg/kg/day.

5. A method according to claim 4, wherein the N,N-dimethylglycine is administered in an amount of 10-100 mg/kg/day.

* * * * *